United States Patent [19]
Paul et al.

[11] Patent Number: 4,916,062
[45] Date of Patent: Apr. 10, 1990

[54] ENZYME, ITS METHOD OF PRODUCTION AND ITS APPLICATION TO THE PREPARATION OF METHYL N-(L-ASPARTYL-1) L-PHENYLALANINATE

[75] Inventors: François Paul; Francis Duchiron; Pierre Monsan, all of Haute-Garonne, France

[73] Assignee: Societe Francaise Hoechst, Puteaux, France

[21] Appl. No.: 921,632

[22] Filed: Oct. 21, 1986

[30] Foreign Application Priority Data

Nov. 5, 1985 [FR] France ............................. 85 16365

[51] Int. Cl.[4] ..................... C12P 21/02; C12M 9/00; C12R 1/265
[52] U.S. Cl. .................................. 435/68.1; 435/183; 435/859
[58] Field of Search ................. 435/70, 859, 183, 219, 435/220

[56] References Cited

U.S. PATENT DOCUMENTS

| 4,086,139 | 4/1978 | Hoerle | 435/220 |
| 4,165,311 | 8/1979 | Isowa et al. | 435/68 |
| 4,666,838 | 5/1987 | Yokozeki et al. | 435/70 |

FOREIGN PATENT DOCUMENTS

| 0074095 | 4/1983 | European Pat. Off. |
| 0124313 | 7/1984 | European Pat. Off. |
| 0154472 | 2/1985 | European Pat. Off. |

OTHER PUBLICATIONS

Dezmazeaud et al., "Facteurs Intervenant dans la Production du Systeme Proteolytique Chez *Micrococcus caseolyticus*", *Ann. Biol. Anim. Bioch. Biophys.*, 1968, 8, (3), pp. 419–429.

Dezmazeaud et al., "Isolement, Purification et Proprietes d'une Protease Exocellulaire de *Micrococcus caseolyticus*", *Ann. Biol. Anim. Bioch. Biophys.*, 1968, 8 (4), pp. 505–577.

Mazur et al., "Structure—Taste Relationships of Some Dipeptides", *J. Am. Chem. Soc.*, 91:10, May 7, 1969, pp. 2684–2691.

Dezmazeaud et al., "Specifite de la protease neutre de *Micrococcus caseolyticus*", *Eur. J. Biochem.*, vol. 19 (1971), pp. 51–55.

Primary Examiner—Charles F. Warren
Assistant Examiner—Gail Knox
Attorney, Agent, or Firm—Browdy and Neimark

[57] ABSTRACT

A polymeric enzyme having a molecular weight higher than or equal to 200,000 and not exhibiting any proteolytic activity on casein derived from a culture of *Micrococcus caseolyticus* is disclosed, as is a method of producing the enzyme by filtration on gel buffered with an aqueous buffer of an enzymatic system prepared by lyophilization of an aqueous concentrate formed by ultrafiltration of the solution obtained by dissolving, in an aqueous solution of calcium chloride, an enzymatic system precipitated from a supernatant of a microorganism culture broth by ammonium sulphate, wherein the enzyme is not retained on a gel calibrated for proteins with a molecular weight of between 5,000 and 20,000, buffered with a 20 mM TRIS-HCl buffer, at pH 7.5, containing 1.5 mM calcium chloride, and the enzymatic system is derived from a culture broth of said *Micrococcus caseolyticus*. The enzyme may be used for the production of aspartame by condensation of L-aspartic acid with methyl DL-phenylalaninate.

2 Claims, No Drawings

ENZYME, ITS METHOD OF PRODUCTION AND ITS APPLICATION TO THE PREPARATION OF METHYL N-(L-ASPARTYL-1) L-PHENYLALANINATE

BACKGROUND OF THE INVENTION

1. Field of the Invention

The present invention relates to a new enzyme, its method of production and its application to the preparation of methyl N-(L-aspartyl-1) L-phenylalaninate.

Enzymatic processes are currently being used to an ever increasing extent to obtain substances having a physiological activity. These enzymatic processes are convenient and, very often, they provide directly the required product with the desired configuration, without it being necessary to carry out separation of enantiomers or diastereoisomers.

2. Description of the Prior Art

Methyl N-(L-aspartyl-1) L-phenylalaninate, commonly known as aspartime, is a very well known dipeptide which possesses remarkable sweetening properties (R. H. Mazur et al., J. Amer. Chem. Soc., 1969, 91, 2684). It can be obtained directly by enzymatic processes starting from methyl DL-phenylalaninate and L-aspartic acid (European Patent Application Nos. 0 0154 472, 0 124 313 and 0 074 095); however, the productivity of these processes is low. This compound is also generally prepared either by using conventional chemical methods or by hydrogenating cutting of its derivative N-benzyloxy-carbonyl resulting from the enzymatic condensation of methyl DL-phenylalaninate with L-N-benzyloxy-carbonyl aspartic acid.

The Applicants have also developed a method of this type, using a proteolytic system, designated SP, extracted from a culture broth of *Micrococcus caseolyticus*, to obtain N-benzyloxy-carbonyl aspartame starting from L-N-benzyloxy-carbonyl aspartic acid and methyl DL-phenylalaninate.

*Micrococcus caseolyticus*, a micro-organism isolated from cow's milk and a strain of which was deposited at the Collection Nationale de Micro-Organisme at the Institut Pasteur in Paris, under No. 1194 on 28th Apr. 1982, does in fact provide, under certain culture conditions, a proteolytic system, SP, from which it is possible to extract a single neutral exocellular proteolytic protease, with a molecular weight of between 35,000 and 41,000, designed P in the following, exhibiting almost the complete proteolytic activity of the proteolytic system SP (M. Desmazeaud et al., Ann. Bio. Anim. Biochem. Biophys., 1968, 8, 419–429, 565–577 and European J. Biochem. 1971,, 19, 51–55).

SUMMARY OF THE INVENTION

The Applicants have now discovered in this proteolytic system SP a new enzyme, designated E in the following, which is devoid of proteolytic activity on casein and also is able to condense directly and under certain conditions L-aspartic acid with methyl DL-phenylalaninate so as to provide aspartame.

The present invention thus relates to this new enzyme E and to a method of producing it.

DETAILED DESCRIPTION OF THE INVENTION

The enzyme E is a protein having a molecular weight greater than or equal to 200,000 and, by stepwise electrophoresis of an acrylamide gel under denaturing conditions, it has been ascertained that it is a polymeric enzyme (one major band of about 40,000 and two minor bands of about 60,000). Furthermore, it does not hydrolyze casein.

It can be readily obtained by filtration on gel (Séphacryl S 200 Superfine marketed by Pharmacia-France S.A., 78391 Bois d'Arcy, France) buffered with a 20 mM tris (hydroxyethyl)aminomethane buffer (hereinafter designated TRIS)-hydrochloride, at pH 7.5, containing 1.5 mM calcium chloride, of a solution of the proteolytic system SP in the same buffer with elution with this buffer.

Filtration is followed by measurement of the optical density of the eluates at 280 nm and the initial fractions corresponding to a molecular weight greater than or equal to 200,000 are combined and then lyophilized. The enzyme E is thus isolated.

The proteolytic system SP is known and it can be produced, in accordance with the technique described by M. Desmazeaud, by treating with an aqueous solution of ammonium sulphate a culture broth, a pH 7.0, of *Micrococcus caseolyticus*, from which the bacteria have been eliminated by centrifuging, then by dissolving the resulting precipitate in an aqueous solution of sodium chloride and, finally, by lyophilizing this solution after it has been subjected to ultra-filtration. This proteolytic system is currently available from the firm Roussel-Uclaf, Paris, under the brand name "RULACTINE".

The present invention also relates to the application of this enzyme E to the preparation of aspartame by enzymatic means.

According to this application of the present invention, the enzyme E, characterized by its properties and by the method enabling it to be produced, has the surprising feature of providing aspartame economically and easily when it is caused to react, under the normal conditions of enzymatic processes, in a mixture of L-aspartic acid and methyl DL-phenylalaninate.

In accordance with this application, at a temperature of between 10° and 45° C., preferably at 40° C., at a pH of between 4 and 8, and advantageously at a pH of between 5 and 7, in the presence of a buffer mixture adjusted to the same pH value, the enzyme E is caused to react in a solution of L-aspartic acid and methyl DL-phenylalaninate, then the aspartame formed is isolated using known means. Under these reaction conditions, the enzyme E rapidly brings about the peptide condensation of carboxyl in position 1 of L-aspartic acid with the amine function of methyl L-phenylalaninate so as to provide aspartame. In favourable conditions, a quantity of enzyme E is caused to react which is expressed in proteins determined in accordance with the Kalckar method, comprised between 0.1 mg and 100 mg, preferably between 0.5 and 10 mg per millimole of L-aspartic acid used.

The formation of aspartame in the reaction medium may be followed by periodical analysis of a sample by high-pressure liquid chromatography (HPLC). When the concentration of aspartame no longer increases to a significant extent in the reaction medium, the latter is then treated in the normal manner to isolate the aspartame formed.

According to another aspect of the application of the present invention, the enzyme E may be replaced with an equivalent amount of enzyme E of the proteolytic system SP, from which it is extracted. In fact, the other enzymes present in this system, in particular the proteolytic enzyme P, do not interfere with the enzyme E.

The following examples are given by way of example and are not intended to restrict the present invention.

EXAMPLE 1

1.1 Preparation of the proteolytic system according to the operating method as described in French Patent No. 82.07883, published under No. 2 525 865

A solution prepared from 750 kg of water, 20 kg of corn steep liquid, 20 kg of casein peptone, 10 kg of yeast autolysate and 906 g of calcium chloride, the pH of which has been adjusted to 7 by adding caustic soda, is sterilized at 120° C. in a fermentation vessel. The temperature of the sterile medium is brought to 30° C., then 15 liters of a sterile solution of 30% dextrose and 10 liters of broth sediment from a culture of *Micrococcus caseolyticus* (strain No. 1194) are introduced. It is left to ferment for 24 hours at 30° C. whilst being stirred and in sterile air, the pH being held constant for the first 10 hours. After 24 hours, 1,050 liters of raw fermentation broth are recovered, which are centrifuged to eliminate bacteria. 1,000 liters of clear centrifuged medium are thus obtained. 560 kg of ammonium sulphate are added to this centrifuged medium and then, after 30 minutes agitation, 250 g of Hyflosupercel are added. After being left for 24 hours, the supernatant medium is removed and the insoluble fraction obtained in 70 liters of a calcium chloride solution is introduced; after agitation for 15 minutes the solution obtained, namely 82 liters, is filtered and then concentrated by ultrafiltration. After 12 hours, 10.5 liters of a concentrated solution of enzymes is obtained having a proteolytic activity of 50500 U per cubic centimeter. This solution is then lyophilized. 1 kg of proteolytic system SP is isolated having a proteolytic activity of 530 U per milligram.

1.2 Determination of proteolytic activity

The proteolytic activity of the enzymatic system is determined by measuring (variation in optical density at 280 nm) the quantity of casein hydrolyzed by the enzymatic system (fraction which cannot be precipitated by trichloroacetic acid) under standard conditions. This is achieved by comparative determination of the absorbency at 280 nm of the filtrate of two reaction media, one of which is obtained by treating, under stirring for 10 minutes at 30° C., 5 ml of a 1% casein solution in the 50 mM TRIS-HCl buffer, at pH 7.5, containing 1.5 mM calcium chloride, with 50 microliters of a solution of the proteolytic system SP at 2 g per liter in the 50 mM TRIS buffer, at pH 7.5, containing 1.5 mM calcium chloride, followed by the addition, at the end of treatment, of 5 ml of an aqueous solution of 20% trichloroacetic acid, and the other of which, serving as reference, is obtained by mixing the same reagents at the outset, including the aqueous trichloracetic acid solution. One unit of proteolytic activity, designated U, corresponds to an increase in absorbency of 0.001 units per minute.

1.3 Preparation of the enzyme E 1 g of the proteolytic system SP containing 270 mg of total proteins (determined by the Kalckar formula) and having a proteolytic activity of 530 U/mg in 0.1 liter of 20 mM TRIS-HCl buffer, at pH 7.5, containing 1.5 mM calcium chloride is dissolved, then this solution is filtered at a rate of 7.5 milliliters per hour and per square cm of column section on 3 liters of Sephacryl S 200 Superfine gel, marketed by Pharmacia, prepared in the 20 mM TRIS-HCl buffer, at pH 7.5, containing 1.5 mM calcium chloride.

Filtration is followed by measuring the absorbency of the eluates at 280 nm and the first fraction is recovered corresponding to the protein E with a molecular weight higher than or equal to 200,000, then continuing the elution a second fraction is recovered corresponding to the neutral exocellular proteolytic protein, P, with a molecular weight of between 35,000 and 41,000, described by M. Desmazeaud et al. Subsequently, the proteolytic activity on casein of the two enzymes is determined and it is verified that the enzyme E does not have any proteolytic activity but that the latter is to be found entirely in the enzyme P.

After lyophilization of the eluates, 53 mg of protein E and 213 mg of protein P are isolated (determined by the Kalckar formula).

1.4 Preparation of aspartame

A solution is left for 2 hours at 40° C. and contains:
20 mmoles of L-aspartic acid,
20 mmoles of methyl DL-phenylalaninate,
26.5 mg of previously isolated protein E,
in 100 ml of 100 mM MES-NaOH buffer, at pH 5.8, then 5 ml of 2N hydrochloric acid are introduced to stop the condensation and, by high-pressure liquid chromatography on a Bondapack C 18 micro-column (marketed by Millipore Waters, V/lizy, France), UV detection at 254 nm and elution with a mixture of 30 mM potassium phosphate buffer, at pH 6.8, acetonitrile, 85/15 (V/V), 12 mg of aspartame, i.e. 0.041 mmole, are determined in the reaction medium. Note: MES denotes morpholino-2 ethanesulphonic acid.

EXAMPLE 2

Example 1 is repeated, replacing the enzyme E with an equivalent amount of the proteolytic system SP, from which this enzyme E is extracted and, as previously, aspartame is obtained.

EXAMPLE 3

Example 1 is repeated, replacing the enzyme E with an equivalent amount of protein of the enzyme P and aspartame is not obtained.

It is to be understood that the present invention has only been described by way of example and without limitation, and that many modification, particularly insofar as equivalents are concerned, could be made thereto without departing from the scope thereof.

What is claimed is:

1. A partially purified enzyme isolated from the multi-enzyme SP component of *Micrococcus caseolyticus* Strain I 194, deposited at the Institut Pasteur, having a molecular weight of at least 200,000 and not exhibiting any proteolytic activity on casein.

2. A method for producing aspartame comprising condensing L-aspartic acid with methyl DL-phenylalaninate in the presence of a catalytically effective amount of the enzyme of claim 1.

* * * * *